(12) United States Patent
Johansson et al.

(10) Patent No.: US 7,897,577 B2
(45) Date of Patent: Mar. 1, 2011

(54) RECONSTITUTED SURFACTANTS HAVING IMPROVED PROPERTIES

(75) Inventors: Jan Johansson, Parma (IT); Tore Curstedt, Parma (IT); Bengt Robertson, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 67 days.

(21) Appl. No.: 12/131,373

(22) Filed: Jun. 2, 2008

(65) Prior Publication Data
US 2009/0088379 A1    Apr. 2, 2009

(30) Foreign Application Priority Data
Jun. 1, 2007    (EP)    .................................. 07010857

(51) Int. Cl.
*A61K 38/00*    (2006.01)
(52) U.S. Cl. ..................................... 514/21.3
(58) Field of Classification Search ........................ None
See application file for complete search history.

(56) References Cited

U.S. PATENT DOCUMENTS

| | | | |
|---|---|---|---|
| 7,511,011 B2 * | 3/2009 | Curstedt et al. | 514/2 |
| 2005/0176625 A1 | 8/2005 | Curstedt et al. | |
| 2006/0205663 A1 | 9/2006 | Johnson et al. | |
| 2008/0242589 A1 * | 10/2008 | Curstedt et al. | 514/2 |
| 2009/0075892 A1 | 3/2009 | Johansson et al. | |
| 2010/0004173 A1 * | 1/2010 | Johansson et al. | 514/12 |

FOREIGN PATENT DOCUMENTS

| | | |
|---|---|---|
| EP | 1 481 665 | 12/2004 |
| EP | 1 506 234 | 2/2005 |
| WO | 92/22315 | 12/1992 |
| WO | 00/47623 | 8/2000 |
| WO | 03/097695 | 11/2003 |
| WO | 2006/055532 | 5/2006 |

OTHER PUBLICATIONS

Cochrane et al. Pulmonary Surfactant Protein B (SP-B): Structure-Function Relationships. Science. 1991. vol. 254, pp. 566-568.*
Johansson, J., et al., "A Synthetic Surfactant Based on a Poly-Leu SP-C Analog and Phospholipids: Effects on Tidal Volumes and Lung Gas Volumes in Ventilated Immature Newborn Rabbits," J. Appl. Physiol, vol. 95, Nov. 2003, pp. 2055-2063.
Davis, A. J., et al., "Lung Function in Premature Lambs and Rabbits Treated with a Recombinant SP-C Surfactant," Am. J. Respir. Crit. Care Med., vol. 157, 1998, pp. 553-559.
U.S. Appl. No. 12/422,581, filed Apr. 13, 2009, Johansson, et al.
T. Curstedt et al., *Biology of the Neonate*, vol. 87, pp. 332-337 (2005).
D. Wilson, *Exp. Opin. Pharmacother.*, vol. 2 (9), pp. 1479-1493 (2001).
Survanta—beractant suspension, Abbott Laboratories, Inc. pp. 1-7.

* cited by examiner

*Primary Examiner*—Cecilia Tsang
*Assistant Examiner*—Marcela M Cordero Garcia
(74) *Attorney, Agent, or Firm*—Oblon, Spivak, McClelland, Maier & Neustadt, L.L.P.

(57) ABSTRACT

The present invention is directed to a reconstituted surfactant containing a lipid carrier, a polypeptide analog of the native surfactant protein SP-C, and a polypeptide comprising a sequence comprised of repeated units where each unit contains between 3 and 8 hydrophobic amino acid residues and one basic amino acid residue. The invention is also directed to the pharmaceutical compositions thereof and to its use for the prophylaxis and/or treatment of RDS and other respiratory disorders.

19 Claims, 4 Drawing Sheets

FIG. 1

| | Phe | Gly | Ile | Pro | Cys | Cys | Pro | Val | His | Leu | Lys |
|---|---|---|---|---|---|---|---|---|---|---|---|
| NH2 | 1 | | | | 5 | | | | | 10 | |
| | Arg | Leu | Leu | Ile | Val | Val | Val | Val | Val | Val |
| | | | | 15 | | | | | 20 | |
| | Leu | Ile | Val | Val | Val | Ile | Val | Gly | Ala | Leu |
| | | | | 25 | | | | | 30 | |
| | Leu | Met | Gly | Leu | COOH | (SEQ ID NO: 9) |

SEQUENCE LISTING

<160> NUMBER OF SEQ ID NOS: 14

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Met Gly
            20                  25                  30

Leu

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Ile Gly
            20                  25                  30

Leu

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Leu Gly
            20                  25                  30

Leu

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Norleucine

<400> SEQUENCE: 4

Ile Pro Ser Ser Pro Val His Leu Lys Arg Leu Lys Leu Leu Leu Leu
1               5                   10                  15

```
Leu Leu Leu Leu Ile Leu Leu Leu Ile Leu Gly Ala Leu Leu Xaa Leu
            20                  25                  30

Gly Leu

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu
            20                  25                  30

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Leu Leu Leu Leu Lys Leu Leu Leu Lys Leu Leu Leu Leu Lys
1               5                   10                  15

Leu Leu Leu Leu Lys
            20

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Leu Leu Leu Leu Leu Lys Leu Leu Leu Leu Lys Leu Leu Leu
1               5                   10                  15

Leu Leu Lys Leu Leu Leu Leu Leu Lys
            20                  25

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Gly Ile Pro Ser Ser Pro Val His Leu Lys Arg Leu Leu Ile Leu
1               5                   10                  15

Lys Leu Leu Leu Leu Lys Ile Leu Leu Leu Lys Leu Gly Ala Leu Leu
            20                  25                  30

Met Gly Leu
        35

<210> SEQ ID NO 9
<211> LENGTH: 35
```

```
<212> TYPE: PRT
<213> ORGANISM: Homo sapiens

<400> SEQUENCE: 9

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
                20                  25                  30

Met Gly Leu
        35

<210> SEQ ID NO 10
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: May or may not be present
<220> FEATURE:
<221> NAME/KEY: MOD_RES
<222> LOCATION: (5)..(6)
<223> OTHER INFORMATION: Ser or Ser-acyl groups containing 12-22 carbon
      atoms
<220> FEATURE:
<221> NAME/KEY: MOD_RES
<222> LOCATION: (13)..(20)
<223> OTHER INFORMATION: Ile, Leu or norleucine; This region may
      encompass 1-8 amino acid residues
<220> FEATURE:
<221> NAME/KEY: MOD_RES
<222> LOCATION: (21)..(21)
<223> OTHER INFORMATION: Lys, Arg, His, Trp, Phe, Tyr or Orn
<220> FEATURE:
<221> NAME/KEY: MOD_RES
<222> LOCATION: (22)..(40)
<223> OTHER INFORMATION: Ile, Leu or norleucine; This region may
      encompass 1-19 amino acid residues
<220> FEATURE:
<221> NAME/KEY: MOD_RES
<222> LOCATION: (45)..(45)
<223> OTHER INFORMATION: Met, Met oxidized on the sulfur atom, Ile, Leu
      or morleucine
<220> FEATURE:
<221> NAME/KEY: MOD_RES
<222> LOCATION: (45)..(45)
<223> OTHER INFORMATION: Met, Met oxidized on the sulfur atom, Ile, Leu
      or norleucine
<220> FEATURE:
<221> NAME/KEY: MOD_RES
<222> LOCATION: (45)..(47)
<223> OTHER INFORMATION: May or may not be present

<400> SEQUENCE: 10

Phe Gly Ile Pro Ser Ser Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Gly Ala Leu Leu Xaa Gly Leu
                35                  40                  45

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(2)
<223> OTHER INFORMATION: May or may not be present
<220> FEATURE:
<221> NAME/KEY: MOD_RES
<222> LOCATION: (3)..(4)
<223> OTHER INFORMATION: Ser or Ser-acyl groups containing 12-22 carbon
      atoms
<220> FEATURE:
<221> NAME/KEY: MOD_RES
<222> LOCATION: (11)..(11)
<223> OTHER INFORMATION: Ile, Leu or norleucine
<220> FEATURE:
<221> NAME/KEY: MOD_RES
<222> LOCATION: (12)..(12)
<223> OTHER INFORMATION: Lys, Arg, His, Trp, Phe, Tyr or Orn
<220> FEATURE:
<221> NAME/KEY: MOD_RES
<222> LOCATION: (13)..(26)
<223> OTHER INFORMATION: Ile, Leu or norleucine
<220> FEATURE:
<221> NAME/KEY: MOD_RES
<222> LOCATION: (31)..(31)
<223> OTHER INFORMATION: Met, Met oxidized on the sulfur atom, Ile, Leu
      or norleucine
<220> FEATURE:
<221> NAME/KEY: MOD_RES
<222> LOCATION: (31)..(33)
<223> OTHER INFORMATION: May or may not be present

<400> SEQUENCE: 11

Ile Pro Ser Ser Pro Val His Leu Lys Arg Xaa Xaa Xaa Xaa Xaa Xaa
1               5                   10                  15

Xaa Xaa Xaa Xaa Xaa Xaa Xaa Xaa Xaa Xaa Gly Ala Leu Leu Xaa Gly
            20                  25                  30

Leu

<210> SEQ ID NO 12
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Ser or Ser-acyl groups containing 12-22 carbon
      atoms
<220> FEATURE:
<221> NAME/KEY: MOD_RES
<222> LOCATION: (11)..(18)
<223> OTHER INFORMATION: Ile, Leu or norleucine; This region may
      encompass 1-8 amino acid residues
<220> FEATURE:
<221> NAME/KEY: MOD_RES
<222> LOCATION: (19)..(19)
<223> OTHER INFORMATION: Lys, Arg, His, Trp, Phe, Tyr or Orn
<220> FEATURE:
<221> NAME/KEY: MOD_RES
<222> LOCATION: (20)..(38)
<223> OTHER INFORMATION: Ile, Leu or norleucine; This region may
      encompass 1-19 amino acid residues
<220> FEATURE:
<221> NAME/KEY: MOD_RES
<222> LOCATION: (43)..(43)
<223> OTHER INFORMATION: Met, Met oxidized on the sulfur atom, Ile, Leu
      or norleucine
<220> FEATURE:
<221> NAME/KEY: MOD_RES
<222> LOCATION: (43)..(45)
<223> OTHER INFORMATION: May or may not be present

<400> SEQUENCE: 12
```

```
Ile Pro Ser Ser Pro Val His Leu Lys Arg Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Gly Ala Leu Leu Xaa Gly Leu
        35                  40                  45

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Ser or Ser-acyl groups containing 12-22 carbon
      atoms
<220> FEATURE:
<221> NAME/KEY: MOD_RES
<222> LOCATION: (31)..(31)
<223> OTHER INFORMATION: Met, Met oxidized on the sulfur atom, Ile, Leu
      or norleucine
<220> FEATURE:
<221> NAME/KEY: MOD_RES
<222> LOCATION: (31)..(33)
<223> OTHER INFORMATION: May or may not be present

<400> SEQUENCE: 13

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
            20                  25                  30

Leu

<210> SEQ ID NO 14
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Ser or Ser-acyl groups containing 12-22 carbon
      atoms
<220> FEATURE:
<221> NAME/KEY: MOD_RES
<222> LOCATION: (12)..(12)
<223> OTHER INFORMATION: Lys, Arg, His or Orn
<220> FEATURE:
<221> NAME/KEY: MOD_RES
<222> LOCATION: (13)..(16)
<223> OTHER INFORMATION: Leu, Ile, norleucine, Val, Ala, Met or Phe
<220> FEATURE:
<221> NAME/KEY: MOD_RES
<222> LOCATION: (17)..(17)
<223> OTHER INFORMATION: Lys, Arg, His or Orn
<220> FEATURE:
<221> NAME/KEY: MOD_RES
<222> LOCATION: (18)..(21)
<223> OTHER INFORMATION: Leu, Ile, norleucine, Val, Ala, Met or Phe
<220> FEATURE:
```

```
-continued

<221> NAME/KEY: MOD_RES
<222> LOCATION: (22)..(22)
<223> OTHER INFORMATION: Lys, Arg, His or Orn
<220> FEATURE:
<221> NAME/KEY: MOD_RES
<222> LOCATION: (23)..(26)
<223> OTHER INFORMATION: Leu, Ile, norleucine, Val, Ala, Met or Phe
<220> FEATURE:
<221> NAME/KEY: MOD_RES
<222> LOCATION: (27)..(27)
<223> OTHER INFORMATION: Lys, Arg, His or Orn

<400> SEQUENCE: 14

Phe Gly Ile Pro Ser Ser Pro Val His Leu Lys Xaa Xaa Xaa Xaa
1               5                   10                  15

Xaa Xaa Xaa Xaa Xaa Xaa Xaa Xaa Xaa Xaa Xaa Leu Gly Ala Leu Leu
            20                  25                  30

Met Gly Leu
        35
```

RECONSTITUTED SURFACTANTS HAVING IMPROVED PROPERTIES

CROSS REFERENCES TO RELATED APPLICATIONS

This application claims priority to European Patent Application No. 07010857.6, filed on Jun. 1, 2007, which is incorporated herein by reference in its entirety.

BACKGROUND OF THE INVENTION

1. Field of the Invention

The present invention relates to reconstituted surfactants comprising a lipid carrier, and a combination of (i) a polypeptide analog of the native surfactant protein SP-C and (ii) a polypeptide comprising a sequence comprised of repeated units where each unit contains between 3 and 8 hydrophobic amino acid residues and one basic amino acid residue. The present invention also relates to pharmaceutical compositions thereof for use in the prophylaxis and/or treatment of RDS and other respiratory disorders.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

The lung surfactant complex is primarily composed of lipids and contains minor amounts of various proteins. When the level of this complex becomes inadequate levels the lung will not function properly. This syndrome is called Respiratory Distress Syndrome (RDS). RDS commonly affects pre-term infants.

Heretofore, RDS has been effectively treated with modified natural surfactant preparations extracted from animal lungs. Commercially available modified surfactant preparations include: (i) Curosurf, derived from porcine lung, (ii) Infasurf, extracted from calf lung lavage and (iii) Survanta, a chemically modified natural bovine lung extract.

The main constituents of the commercially available surfactant preparations are phospholipids, such as 1,2-dipalmitoyl-sn-glycero-3-phosphocholine, commonly known as dipalmitoylphosphatidylcholine (DPPC); phosphatidylglycerol (PG); and surfactant hydrophobic proteins B and C (SP-B and SP-C).

There are some significant drawbacks in using surfactant preparations from animal tissues. These drawbacks include difficulties arising during complex production and the sterilization process. Further drawbacks include the possible induction of immune reactions. Accordingly, synthetic surfactants mimicking the composition of the modified natural surfactants have been developed. Synthetic surfactants are known as reconstituted surfactants.

The development of clinically active reconstituted surfactants has turned out to be complicated since the native hydrophobic proteins are too big to synthesize, structurally complex and unstable in pure form. In order to replace native hydrophobic proteins, some synthetic polypeptides partially corresponding to their sequences and analogs thereof have been proposed, for example, in WO 89/06657, WO 92/22315, WO 95/32992, U.S. Pat. No. 6,660,833, EP 413,957, WO 91/18015 and WO 00/47623.

In these references, the treatment with reconstituted surfactants in animal studies gives rise to poor lung gas volumes and grade of alveolar patency at the end of expiration. Thus, ventilation is required with a positive end expiratory pressure (PEEP) in order to achieve an in vivo activity comparable to that achieved with modified natural surfactants (Johansson J et al J Appl Physiol 2003, 95, 2055-2063; Davis A J et al Am J Respir Crit Care Med 1998; 157, 553-559).

The reconstituted surfactant preparations available heretofore are indeed not sufficient to form a stable phospholipid film in the alveoli at the end of expiration. As such, there remains an unmet need for a reconstituted surfactant with improved properties in terms of lung compliance. In particular there is a need for a reconstituted surfactant preparation which is able to guarantee alveolar stability, and hence to maintain alveolar stability at the end of expiration without requiring ventilation with PEEP.

SUMMARY OF THE INVENTION

Accordingly, it is one object of the present invention to provide novel a reconstituted surfactant comprising a lipid carrier, and a combination of (i) a polypeptide analog of the native surfactant protein SP-C and (ii) a polypeptide comprising a sequence comprised of repeated units where each unit contains between 3 and 8, preferably from 4 to 5, hydrophobic amino acid residues and one basic amino acid residue.

In particular it is one object of the present invention to provide a novel reconstituted surfactant comprising:

a) a lipid carrier;

b) a polypeptide analog of the native surfactant protein SP-C, which has at least 20 amino acid residues and no more than 40 amino acid residues and has the sequence represented by formula (I):

(SEQ ID NO: 10)

wherein:

X is an amino acid residue independently selected from the group consisting of I, L, and nL;

B is an amino acid residue independently selected from the group consisting of K, R, H, W, F, Y, and Orn;

S is optionally substituted with acyl groups containing 12-22 carbon atoms, preferably 16 carbon atoms, linked to the side chain via an ester bond;

Ω is an amino acid residue selected from the group consisting of M or M oxidized on the sulfur atom, I, L, and nL;

a is an integer having a value comprised from 1 to 8;

b is an integer having a value comprised from 1 to 19;

e, f, g and p are integers having a value of 0 or 1;

with the proviso that $X_aBX_b$ is a sequence having a maximum of 22 amino acids;

c) a polypeptide comprising a sequence composed of repeated units where each unit contains between 3 and 8 hydrophobic amino acid residues and one basic amino acid residue, preferably a polypeptide of at least 12 amino acid residues and no more than 60 amino acid residues, and having the sequence represented by the formula (II)

(II)

wherein
- U is an amino acid residue independently selected from the group consisting of L, I, nL, V, A, M and F;
- B is an amino acid residue independently selected from the group consisting of K, R, H, and Orn;
- a is an integer having a value comprised between 3 and 8, preferably from 4 to 6; and
- x is an integer having a value comprised between 2 and 6, preferably from 3 to 4.

It is another object of the present invention to provide novel pharmaceutically acceptable salts of said polypeptides and their blocked N- and/or C-terminus derivatives, e.g via acetylation and amidation.

It is another object of the present invention to provide novel pharmaceutical compositions comprising the reconstituted surfactant of the invention.

It is yet another object of the present invention to provide a novel use of the reconstituted surfactant described herein as a medicament.

It is still yet another object of the present invention to provide a method for employing the novel reconstituted surfactant described herein for the prophylaxis and/or treatment of respiratory distress syndrome (RDS) in prematurely born babies, diseases related to a surfactant-deficiency or dysfunction, and other respiratory disorders.

In still a further object of the present invention is a method of preventing and/or treating respiratory distress syndrome (RDS) in prematurely born babies, diseases related to a surfactant-deficiency or dysfunction and other respiratory disorders, said method comprising the administration of an effective amount of the reconstituted surfactant described before.

Thus, the present invention provides:

[1] A reconstituted surfactant comprising
(a) a lipid carrier;
(b) an analog of the native surfactant protein SP-C, wherein said analog of the native surfactant protein SP-C is a polypeptide having 20 to 40 amino acid residues comprising the sequence represented by formula (I)

$$F_eG_eI_fP_fS_gSPVHLKRX_aBX_bGALL\Omega_pG_pL_p \quad (I)$$
(SEQ ID NO: 10)

wherein:
- X is an amino acid residue independently selected from the group consisting of I, L, and nL,
- B is an amino acid residue independently selected from the group consisting of K, R, H, W, F, Y, and Orn,
- S is S or S substituted with one or more acyl groups containing 12-22 carbon atoms linked to the side chain of S via an ester bond,
- Ω is an amino acid residue selected from the group consisting of M or M oxidized on the sulfur atom, I, L, and nL,
- a is an integer ranging from 1 to 8,
- b is an integer ranging from 1 to 19,
- e, f, g and p are integers independently selected from 0 or 1,
- with the proviso that $X_aBX_b$ is a sequence having a maximum of 22 amino acids; and
(c) a polypeptide having 12 to 60 amino acid residues and comprising a sequence composed of repeated units where each unit contains between 3 and 8 hydrophobic amino acid residues and one basic amino acid residue, wherein the polypeptide has the sequence represented by formula (II)

$$B(U_aB)_x \quad (II)$$

wherein
- U is an amino acid residue independently selected from the group consisting of L, I, nL, V, A, M and F,
- B is an amino acid residue independently selected from the group consisting of K, R, H, and Orn,
- a is an integer ranging from 3 to 8, and
- x is an integer ranging from 2 to 6.

[2] The reconstituted surfactant according [1], wherein a in formula (II) is an integer ranging from 4 to 6.

[3] The reconstituted surfactant according to [1], wherein x in formula (II) is an integer ranging from 3 to 4.

[4] The reconstituted surfactant according to [1], wherein the analog of the native surfactant protein SP-C is represented by formula (Ia)

$$I_pP_fSSPVHLKRX_aBX_bGALL\Omega_pG_pL_p \quad (Ia)$$
(SEQ ID NO: 11)

wherein
- a is 1;
- b is 14; and
- f and p are 0 or 1.

[5] The reconstituted surfactant according to [1], wherein the analog of the native surfactant protein SP-C is represented by formula (Ib)

$$IPSSPVHLKRX_aBX_bGALL\Omega_pG_pL_p \quad (Ib)$$
(SEQ ID NO: 12)

wherein p is 0 or 1.

[6] The reconstituted surfactant according to [1], wherein the analog of the native surfactant protein SP-C is represented by formula (Ic)

$$IPSSPVHLKRLKLLLLLLLLILLLILGALL\Omega_pG_pL_p \quad (Ic)$$
(SEQ ID NO: 13)

wherein p is 0 or 1.

[7] The reconstituted surfactant according to [1], wherein the analog of the native surfactant protein SP-C is selected from the group consisting of:

| | |
|---|---|
| IPSSPVHLKRLKLLLLLLLLILLLILGALLMGL | (SEQ ID NO: 1) |
| IPSSPVHLKRLKLLLLLLLLILLLILGALLIGL | (SEQ ID NO: 2) |
| IPSSPVHLKRLKLLLLLLLLILLLILGALLLGL | (SEQ ID NO: 3) |
| IPSSPVHLKRLKLLLLLLLLILLLILGALLnLGL, and | (SEQ ID NO: 4) |
| IPSSPVHLKRLKLLLLLLLLILLLILGALL. | (SEQ ID NO: 5) |

[8] The reconstituted surfactant according to [1], wherein the polypeptide of formula (II) has a sequence represented by formula (III)

$$B(U_4B)_x \quad (III)$$

wherein
- U is an amino acid residue independently selected from the group consisting of L and I;
- B is an amino acid residue independently selected from the group consisting of K and R; and
- X is an integer having a value of 3 or 4.

[9] The reconstituted surfactant according to [8], wherein X in formula (III) is 4.

[10] The reconstituted surfactant according to [8], wherein the polypeptide has the formula KLLLLKLLLLKLLLLKLLLLK (SEQ ID NO:6).

[11] The reconstituted surfactant according to [1], wherein the analog of the native surfactant protein SP-C has the formula IPSSPVHLKRLKLLLLLLLLILLLILGALLLGL (SEQ ID NO: 3); and the polypeptide comprising a sequence of repeated units has the formula KLLLLKLLLLKLLLLKLLLLK (SEQ ID NO:6).

[12] The reconstituted surfactant according to [1], wherein each polypeptide of formulae (I) and (II) is present in an amount ranging from 0.5 to 10% based on the weight of the surfactant (w/w).

[13] The reconstituted surfactant according to [1], wherein each polypeptide of formulae (I) and (II) is present in an amount ranging from 1 to 5% based on the weight of the surfactant (w/w).

[14] The reconstituted surfactant according to [1], wherein each polypeptide of formulae (I) and (II) is present in an amount ranging from 1 to 3% based on the weight of the surfactant (w/w).

[15] The reconstituted surfactant according to [1], wherein the lipid carrier is at least one phospholipid selected from the group consisting of a phosphatidylcholine, a phosphatidylglycerol, a phosphatidylinositol, a phosphatidylethanolamine, a phosphatidylserine, and a sphingomyelin.

[16] The reconstituted surfactant according to [1], wherein the lipid carrier comprises a mixture of phospholipids.

[17] The reconstituted surfactant according to [16], wherein the mixture of phospholipids consists of (a) dipalmitoylphosphatidylcholine and (b) a palmitoyloleoylphospholipid selected from the group consisting of palmitoyloleoylphosphatidylglycerol and a mixture of palmitoyloleoylphosphatidylglycerol with palmitoyloleoylphosphatidylcholine, in a weight ratio ranging from 95:5 to 50:50.

[18] The reconstituted surfactant according to [17], wherein the phospholipid mixture consists of dipalmitoylphosphatidylcholine and palmitoyloleoylphosphatidylglycerol in a weight ratio of 68:31.

[19] The reconstituted surfactant according to [17], wherein the (a) is in an amount ranging from 90 to 99% by weight based on the total weight of the surfactant, and the sum of (b) and (c) ranges from 1 to 10% by weight based on the total weight of the surfactant.

[20] A pharmaceutical composition comprising the reconstituted surfactant according to [1] and a pharmaceutically acceptable carrier or excipient.

[21] The pharmaceutical composition according to [20], which is in the form of a solution, dispersion, suspension or dry powder.

[22] The pharmaceutical composition according to [20], which is in the form of an aqueous suspension.

[23] The pharmaceutical composition according to [20], comprising the reconstituted surfactant in a concentration ranging from 2 and 160 mg/ml.

[24] The pharmaceutical composition according to [20], comprising the reconstituted surfactant in a concentration ranging from 20 and 80 mg/ml.

[25] A method of treating respiratory distress syndrome (RDS) in prematurely born babies comprising administering to a subject in need thereof an effective amount of the reconstituted surfactant according to [1].

[26] A method of treating a disease related to a surfactant-deficiency or dysfunction comprising administering to a subject in need thereof an effective amount of the reconstituted surfactant according to [1].

[27] The method according to [26], wherein the disease related to a surfactant-deficiency or dysfunction is selected from the group consisting of acute lung injury (ALI), RDS in adults (ARDS), meconium aspiration syndrome (MAS), and bronchopulmonary dysplasia (BPD).

[28] A method of preventing respiratory distress syndrome (RDS) in prematurely born babies comprising administering to a subject in need thereof an effective amount of the reconstituted surfactant according to [1].

[29] A method of preventing a disease related to a surfactant-deficiency or dysfunction comprising administering to a subject in need thereof an effective amount of the reconstituted surfactant according to [1].

[30] The method according to [29], wherein the disease related to a surfactant-deficiency or dysfunction is selected from the group consisting of acute lung injury (ALI), RDS in adults (ARDS), meconium aspiration syndrome (MAS), and bronchopulmonary dysplasia (BPD).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the amino acid sequence of human protein SP-C (SEQ ID NO: 8).

DETAILED DESCRIPTION OF THE PREFERRED EMBODIMENTS

Figure 2:
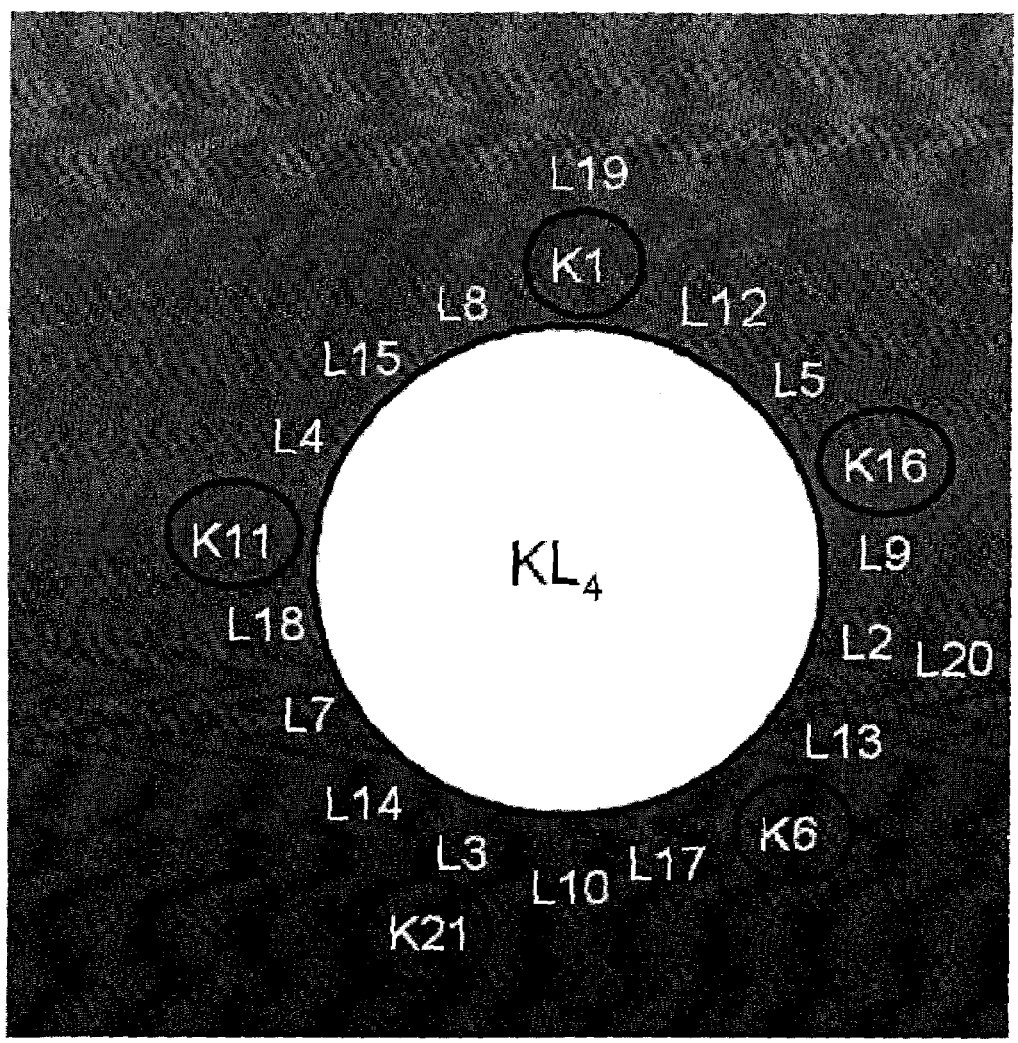
FIG. 2 shows the helical wheel representation of the polypeptide $KL_4$. The basic amino acid residues are circled.

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In view of the difficulties heretofore existing in the art with respect to reconstituted surfactants preparations, the present inventors sought to overcome such challenges. Against this background, the present inventors surprisingly discovered that the objects of the present invention can be met by providing a reconstituted surfactant preparation with improved properties in terms of lung compliance, and in particular, in terms of capacity to effectively maintain alveolar patency at the end of expiration without requiring ventilation with PEEP. Specifically, the present inventors have surprisingly found that this object is achieved by a combination of a particular polypeptide analog of the native SP-C protein and a polypeptide comprising a sequence composed of repeated units where each unit contains between 3 and 8 hydrophobic amino acid residues and one basic amino acid residue. In a model of RDS wherein the immature newborn were treated with exogenous surfactant preparations without applying PEEP, a combination of said polypeptides acts on the lung gas volumes which is an index of the alveolar patency at the end of expiration.

In the relevant art, respiratory function after in vivo treatment with the exogenous surfactant preparations is carried out by measuring two parameters:

i) the tidal volume which is an index of the lung compliance and ii) the lung gas volume which is an index of the alveolar air expansion or patency at the end of expiration, and hence of the capability of forming a stable phospholipid film in the alveoli at the end of expiration.

As used herein, an effective amount of a compound for treating a particular disease is an amount that is sufficient to ameliorate, or in some manner reduce the symptoms associated with the disease. Said amount will depend on the kind and the severity of the disease and the conditions (weight, sex, age) of the patient.

As used herein, the term "reconstituted surfactant" means a lipid carrier to which polypeptide analogs of the surfactant proteins, made through recombinant technology or synthetic methods, have been added.

As used herein, the term "lipid carrier" means a mixture of phospholipids and optionally further lipid components, for example neutral lipids such as triacylglycerols, free fatty acids and/or cholesterol.

As used herein, the term "polypeptide analog of the native surfactant protein SP-C", includes polypeptides having an amino acid sequence in which, compared to the native proteins, one or more amino acids have been deleted, have been inserted, have been added, or have been replaced (i.e., mutated) by other amino acids, so long as the polypeptides, in a mixture with a lipid carrier, show pulmonary surfactant activity. In this context, the term "one or more" includes 1 to 10 amino acids, including all integers and sub-ranges there between, preferably 1 to 5 amino acids, including all integers and sub-ranges there between, more preferably 1 to 3 amino acids, including all integers and sub-ranges there between, and most preferably 1 or 2 amino acids.

As is conventional in the art, the amino acid sequences herein are shown according to the three-letter code with the amino acid which carries the free amino group at the left end (amino terminus) and the amino acid which carries the free carboxyl group at the right end (carboxy terminus). All the amino acid residues identified herein are in the natural L-configuration and the sequences identified herein are reported according to standard abbreviations for amino acid residues as shown in Table I.

Table I

| Amino Acid | Symbol | |
|---|---|---|
| | One-Letter | Three-letter |
| Glycine | G | Gly |
| L-proline | P | Pro |
| L-isoleucine | I | Ile |
| L-leucine | L | Leu |
| L-tyrosine | Y | Tyr |
| L-cysteine | C | Cys |
| L-tryptophan | W | Trp |
| L-alanine | A | Ala |
| L-lysine | K | Lys |
| L-arginine | R | Arg |
| L-glutamine | Q | Glu |
| L-methionine | M | Met |
| L-serine | S | Ser |
| L-valine | V | Val |
| L-asparagine | N | Asn |

Table I-continued

| Amino Acid | Symbol | |
|---|---|---|
| | One-Letter | Three-letter |
| L-aspartic acid | D | Asp |
| L-glutamic acid | E | Glu |
| L-histidine | H | His |
| L-threonine | T | Thr |
| L-phenylalanine | F | Phe |
| L-nor-leucine | — | nLeu |
| L-ornithine | — | Orn |

The present invention is directed to a reconstituted surfactant comprising a lipid carrier and a combination of (i) a polypeptide analog of the native surfactant protein SP-C and (ii) a polypeptide comprising a sequence comprised of repeated units where each unit contains between 3 and 8, preferably from 4 to 5, hydrophobic amino acid residues and one basic amino acid residue.

The present inventors have discovered that, in a model of RDS wherein the immature newborn were treated with exogenous surfactant preparations without applying PEEP, polypeptides of formula (I), in combination with polypeptides of formula (II), provide substantial benefits with respect to lung gas volume, which is an index of the alveolar patency at the end of expiration. Indeed, the reconstituted surfactant preparation of the present invention improves the respiratory function as expressed by the tidal volumes to an extent comparable with that achieved after administration of a modified natural surfactant.

Advantageously, the analog of the native protein SP-C is a polypeptide having at least 20 amino acid residues and no more than 40 amino acid residues, and having the sequence represented by the formula (I)

$$F_e G_e I_f P_f S_g SPVHLKRX_a BX_b GALL\Omega_p G_p L_p \quad (I)$$
(SEQ ID NO: 10)

wherein:

X is an amino acid residue independently selected from the group consisting of I, L, and nL;

B is an amino acid residue independently selected from the group consisting of K, R, H, W, F, Y, and Orn;

S is optionally substituted with acyl groups containing 12-22 carbon atoms, preferably 16 carbon atoms, linked to the side chain via an ester bond;

$\Omega$ is an amino acid residue selected from the group consisting of M or M oxidized on the sulfur atom, I, L, and nL;

a is an integer having a value comprised from 1 to 8;

b is an integer having a value comprised from 1 to 19;

e, f, g and p are integers having a value of 0 or 1;

with the proviso that $X_a BX_b$ is a sequence having a maximum of 22 amino acids.

Preferably, $X_a BX_b$ is a sequence having between 10 and 22 amino acids.

Preferably, the polypeptide of formula (I) is composed of at least 30 and no more than 35 amino acids, more preferably no more than 33 amino acids.

In particular embodiments the polypeptides of formula (I) is composed of 30 or 33 or 35 amino acids.

In an embodiment of the present invention, the polypeptide analog of the SP-C protein is represented by formula (Ia) in which e and n are 0, and g is 1

$$I_fP_fSSPVHLKRX_aBX_bGALL\Omega_pG_pL_p \quad (Ia)$$
(SEQ ID NO: 11)

wherein
X, B and Ω are as defined above;
a is 1;
b is 14;
f and p are 0 or 1.

In another embodiment of the present invention, the polypeptide analog of the SP-C protein is represented by formula (Ib) in which f is 1

$$IPSSPVHLKRX_aBX_bGALL\Omega_pG_pL_p \quad (Ib)$$
(SEQ ID NO: 12)

wherein:
X, B, Ω, a and b are as defined above;
p is 0 or 1.

In yet another embodiment of the present invention, the polypeptide analog of the SP-C protein is represented by formula (Ic)

$$IPSSPVHLKRLKLLLLLLLLILLLILGALL\Omega_pG_pL_p \quad (Ic)$$
(SEQ ID NO: 13)

wherein:
Ω is as defined above
p is 0 or 1.

Examples of polypeptides of formula (Ic) include:

```
                                          (SEQ ID NO: 1)
IPSSPVHLKRLKLLLLLLLLILLLILGALLMGL                 (Id)

(SEQ ID NO: 2)
IPSSPVHLKRLKLLLLLLLLILLLILGALLIGL                 (Ie)

(SEQ ID NO: 3)
IPSSPVHLKRLKLLLLLLLLILLLILGALLLGL                 (If)

(SEQ ID NO: 4)
IPSSPVHLKRLKLLLLLLLLILLLILGALLnLGL                (Ig)

(SEQ ID NO: 5)
IPSSPVHLKRLKLLLLLLLLILLLILGALL                    (Ih)
```

The polypeptide analog of the SP-C protein represented by formula (Id) has been referred to as SP-C33.

Thus, of the polypeptide analogs of the SP-C protein represented by formula (I), preferable polypeptides include those selected from the group of polypeptides having the formulae (Ie), (If), (Ig) and (Ih), of which the most preferred polypeptide is formula (If).

In the present invention, the polypeptide comprising a sequence composed of repeated units where each unit contains between 3 and 8 hydrophobic amino acid residues and one basic amino acid residue, preferably a polypeptide of at least 12 amino acid residues and no more than 60 amino acid residues, preferably of least 20 and no more than 35, is represented by formula (II)

$$B(U_aB)_x \quad (II)$$

wherein
U is an amino acid residue independently selected from the group consisting of L, I, nL, V, A, M and F;
B is an amino acid residue independently selected from the group consisting of K, R, H, and Orn;
a is an integer having a value comprised between 3 and 8, preferably from 4 to 6, more preferably 4 to 5, even more preferably 4; and
x is an integer having a value comprised between 2 and 6, preferably from 3 to 4, more preferably 4.

In an embodiment of the present invention, are polypeptides that comprise or consist of a sequence of formula (II) wherein U is L or I, B is K or R, a is 4 or 5, preferably 4, and x 3 or 4, preferably 4.

In another embodiment of the present invention, the polypeptide of formula (II) has the sequence referred to as $KL_4$ and which has the sequence:

```
KLLLLKLLLLKLLLLKLLLLK   (KL4)    (SEQ ID NO: 6)
```

In yet another embodiment of the present invention, the polypeptide of formula (II) has the sequence referred to as $KL_5$ and which has the sequence:

```
KLLLLLKLLLLLKLLLLLKLLLLLK   (KL5)   (SEQ ID NO: 7)
```

It has indeed been found that $KL_5$ shows a distribution of the charged residues around the entire helical circumference of the peptide similar to that of $KL_4$.

Thus, in an embodiment of the present invention, the polypeptide of formula (II) may have the sequence represented by formula (III)

$$B(U_4B)_x \quad (III)$$

wherein
U is an amino acid residue independently selected from the group consisting of L and I;
B is an amino acid residue independently selected from the group consisting of K and R; and
X is an integer having a value of 3 or 4, preferably 4.

In the context of formulae (II) and (III), the phrase, "the polypeptide comprising a sequence composed of repeated units where each unit contains between 3 and 8 hydrophobic amino acid residues and one basic amino acid residue, preferably a polypeptide of at least 12 amino acid residues and no more than 60 amino acid residues, preferably of least 20 and no more than 35" is understood to mean that the polypeptide may be specifically restricted to the polypeptide of formulae (II) and (III) (i.e., the polypeptide consists of the sequence defined in these formulae without additional residues at the N or C termini) or may include additional N and/or C terminal amino acid residues of varying sequence.

Thus, further examples of polypeptides within the scope of formula (II) are those having the sequence (IV):

```
FGIPSSPVHLKBU4BU4BU4BLGALLMGL        (IV)
(SEQ ID NO: 14)
``` wherein:
B and U are as defined above.

An example of polypeptide of formula (IVa) is referred to as SP-C (LKS) and has the formula:

(SEQ ID NO: 8)
FGIPSSPVHLKRLLILKLLLLKILLLKLGALLMGL[SP-C(LKS)].

The polypeptides of formulae (I)-(III) may be prepared by any technique known to those skilled in the art such as those described in J. M. Steward and J. D. Young, "Solid Phase Peptide Synthesis", W.H. Freeman Co., San Francisco, 1969, and J. Meienhofer, Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis. A summary of polypeptide synthesis techniques may be found in J. Stuart and J. D. Young, Solid Phase Peptide Synthesis, Pierce Chemical Company, Rockford, Ill., 3d Ed., Neurath, H. et al., Eds., p. 104-237, Academic Press, New York, N.Y. (1976).

Appropriate protective groups for use in such syntheses will be found in the above texts as well as in J. F. W. McOmie, Protective Grouts in Organic Chemistry, Plenum Press, New York, N.Y. (1973).

In general, these methods comprise the sequential addition of one or more amino acid residues or suitably protected amino acid residues to a growing peptide chain. Typically, either the amino or carboxyl group of the first amino acid residue is protected by a suitable, selectively removable protecting group.

By way of example, the protected or derivatized amino acid is attached to an inert solid support through its unprotected carboxyl or amino group. The amino- or carboxyl-protecting group is then selectively removed and the next amino acid in the sequence having the complementary (amino or carboxyl) group suitably protected is admixed and reacted under conditions suitable for forming the amide linkage with the residue already attached to the solid support. The amino- or carboxyl-protecting group is then removed from this newly added amino acid residue, and the next amino acid (suitably protected) is then added, and so forth.

After all the desired amino acids have been linked in the proper sequence, any remaining terminal and side group protecting groups (and solid support) are removed sequentially or concurrently, to obtain the final polypeptide.

In particular the polypeptides of formulae (I) and (IV) may be prepared according to the methods disclosed in WO 00/47623. The polypeptides consisting of a sequence of formulae (II) and (III) may be prepared according to the methods described in WO 92/22315.

The reconstituted surfactant of the invention may be prepared by mixing a solution or a suspension of the polypeptides of formulae (I) and (II) and lipids and by subsequently drying the mixture, otherwise they may be prepared by lyophilisation or spray-drying.

Preferably, the polypeptides of general formula (I) and the polypeptides of formula (II) are present in the reconstituted surfactants of the invention in a fixed amount and quantitative ratio as a fixed combination.

The proportion of the polypeptides of formulae (I) and (II) to the reconstituted surfactant can vary. Advantageously, each polypeptide may be present in an amount of between 0.5 and 10% based on the weight of the surfactant (w/w), preferably between 1 and 5%, most preferably between 1 and 3%.

Advantageously, the lipid carrier comprises one or more of the phospholipids that are contained in natural pulmonary surfactant preparations, for example phosphatidylcholines (PC) such as dipalmitoylphosphatidylcholine (DPPC) and palmitoyloleoylphosphatidylcholine (POPC), and phosphatidylglycerols (PG), such as palmitoyloleoylphosphatidylglycerol (POPG) and dipalmitoylposphatidylglycerol (DPPG).

Other phospholipids which can be advantageously used are phosphatidylinositols (PI), phosphatidylethanolamines (PE), phosphatidylserines and sphingomyelins (SM). In a particular embodiment, the lipid carrier may comprise further components, for example neutral lipids such as triacylglycerols, free fatty acids and/or cholesterol.

In an embodiment of the present invention, the mixture of phospholipids forming the lipid carrier contains (a) dipalmitoylphosphatidylcholine and (b) a palmitoyloleoylphospholipid selected from the group consisting of palmitoyloleoylphosphatidylglycerol and a mixture of palmitoyloleoylphosphatidylglycerol with palmitoyloleoylphosphatidylcholine, in a weight ratio ranging from 95:5 to 50:50. Preferably, the mixture of phospholipids forming the lipid carrier contains dipalmitoylphosphatidylcholine and palmitoyloleoylphosphatidylglycerol in a weight ratio of 68:31.

In an embodiment of the present invention, the reconstituted surfactant according to the invention comprises 90 to 99% by weight of the lipid carrier, preferably 92 to 98%, more preferably 94 to 96%, and 1 to 10% by weight of the sum of both peptides, preferably 2 to 8%, more preferably 4 to 6%.

In another embodiment of the present invention, the reconstituted surfactant comprises 96% by weight of a lipid carrier, 2% by weight of a polypeptide of formula (I) and 2% by weight of a polypeptide of formula (II).

In an embodiment of the present invention, the phospholipids contained in the lipid carrier are preferably mixtures consisting of DPPC and a palmitoyloleylphospholipid selected from POPG or a mixture thereof with POPC in weight ratios ranging from 95:5 to 50:50, preferably from 80:20 to 60:40. The weight ratio of DPPC to POPG ranges preferably from 75:25 to 65:35, and is more preferably 68:31. In the case of DPPC:POPG:POPC mixtures, the phospholipids are preferably used in weight ratios of 60:20:20 or 68:15:16.

In another embodiment of the present invention, the reconstituted surfactant comprises from 1 to 5% by weight of a polypeptide of formula (Ia), from 1 to 5% by weight of a polypeptide of formula (II) and a mixture of DPPC and POPG in a weight ratio of 68:31.

In yet another embodiment of the present invention, the reconstituted surfactant comprises from 1.5 to 3% by weight of a polypeptide selected from the group consisting of (Ie), (If), (Ig) and (Ih), more preferably the polypeptide (If), from 1.5 to 3% by weight of a peptide of formula (II) and a mixture of DPPC and POPG in a weight ratio of 68:31.

In another embodiment of the present invention, the reconstituted surfactant of the present invention may be packaged in a pharmaceutical composition wherein the reconstituted surfactant admixed with a pharmaceutically acceptable carrier or excipient.

The administration of the reconstituted surfactant of the invention is carried out in a manner known to the skilled artisan, preferably by intratracheal instillation (infusion or bolus) or by nebulisation.

The effective dose of the reconstituted surfactant varies depending upon many different factors including means of administration, type and severity of the disease and whether the treatment is prophylactic or therapeutic. In general, the dose is comprised between 0.01 mg and 10 g per kg of body weight, preferably between 10 and 500 mg per kg, more preferably between 40 and 200 mg per kg. The skilled artisan can easily determine the optimum dose and frequency of administration thereof. Specifically, the dose regimen for the methods of the present invention will depend on the severity of the disease if mild, moderate or severe and on the patient's age, sex, weight, etc. The dosing can include administration of a single unit dosage form or a multi-dosing in divided dosage forms.

The present invention also relates pharmaceutical compositions comprising the reconstituted surfactant of the invention. Said compositions are advantageously administered in the form of a solution, dispersion, suspension or dry powder. Preferably said compositions comprise the reconstituted surfactant dissolved or suspended in a suitable solvent or resuspension medium.

Preferably said pharmaceutical compositions are supplied as suspension in a buffered physiological saline aqueous solution in single-use glass vials. Advantageously the reconstituted surfactant concentration (expressed as phospholipid content) is in the range of from about 2 to about 160 mg of surfactant per ml, preferably between 10 and 100 mg/ml, more preferably between 20 and 80 mg/ml.

To achieve a lower viscosity, said compositions may further comprise electrolytes, such as calcium, magnesium and/or sodium salts (for example calcium chloride or sodium chloride).

The pharmaceutical compositions according to the present invention are suitable for the prophylaxis (i.e., prevention) and/or treatment of respiratory distress syndrome (RDS) in prematurely born babies or other diseases related to a surfactant-deficiency or dysfunction including acute lung injury (ALI), RDS in adults (ARDS), meconium aspiration syndrome (MAS), and bronchopulmonary dysplasia (BPD).

The pharmaceutical compositions according to the present invention also suitable for the prophylaxis (i.e., prevention) and/or treatment of other respiratory disorders such as pneumonia, bronchitis, COPD (chronic obstructive pulmonary disease), asthma, and cystic fibrosis as well as for the treatment of serous otitis media (glue ear).

In addition to be used of the prophylaxis (i.e., prevention) and/or treatment of the above-recited disorders, the reconstituted surfactant of the present invention may also be administered to ameliorate the symptoms of the recited disorders, alleviate the intensity of the symptoms of the recited disorders, and reduce the propensity of the subject from developing symptoms associated with the recited disorders. Further, within the context of the present invention, the reconstituted surfactant of the present invention may be administered to a subject after having received a clinical diagnosis of having one or more of the above-recited disorders or administered as a precaution to a subject at risk of developing one or more of the above-recited disorders.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of" "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

In Vivo Experiments with a Reconstituted Surfactant Based on the Polypeptides SP-C33 and $KL_4$ Surfactant preparations were assayed in premature newborn rabbits, obtained by hysterectomy at the gestational age of 27 days. The experiments were performed without applying a positive end expiratory pressure (PEEP).

As SP-C analog, the polypeptide referred to as SP-C33 having the sequence of IPSSPVHLKRLKLLLLLLLLILL-LILGALLMGL (SEQ ID NO: 1) was used which was prepared in accordance with the protocol described in WO 00/47623.

As analog of the protein SP-B, the polypeptide referred to as $KL_4$ was used which was prepared according to WO 92/22315. KL4 has the sequence of KLLLLKLLLLKLLLLKLLLLK (SEQ ID NO: 6).

The animals were treated at birth with 200 mg/kg (80 mg/ml) of reconstituted surfactant preparations containing 2% SP-C33 or 2% SP-C33+2% $KL_4$ in combination with a phospholipid mixture consisting of DPPC:POPG in the ratio 68:31 w/w.

Animals treated with Curosurf® (80 mg/ml) served as positive controls and non-treated littermates as negative controls.

The immature newborn rabbits were ventilated in parallel with a standardized sequence of peak insufflation pressures. To open up the lungs, pressure was first set at 35 $cmH_2O$ for 1 min. After this recruitment manoeuvre, pressure was lowered to 25 $cmH_2O$ for 15 min and further on to 20 and 15 cm $H_2O$. Finally, pressure was raised again to 25 $cmH_2O$ for 5 min, after which the lungs were ventilated for additional 5 min with nitrogen and then excised for gas volume measurements.

Figure 4:
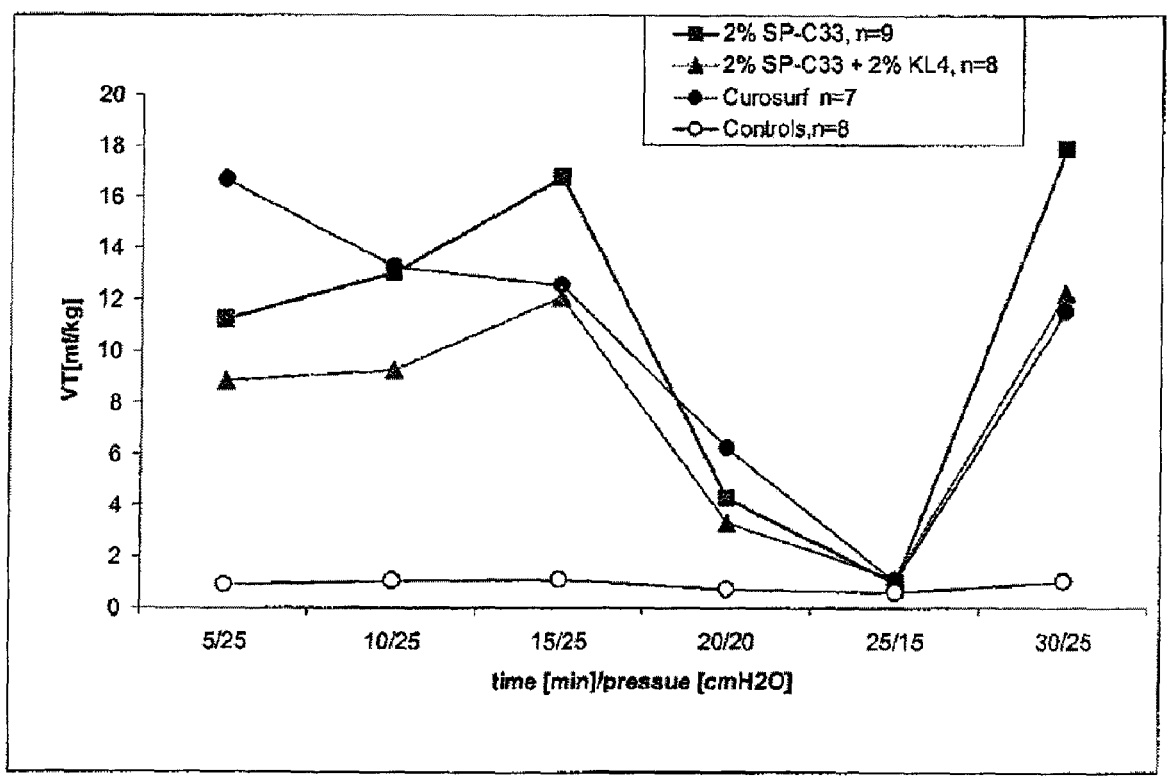
FIG. 4 shows the results in terms of tidal volumes (ml/kg) as a function of time/pressure.

Both lung gas volumes and tidal volumes expressed as ml/kg were measured and the results, given as median values, are reported in FIGS. 4 and 5, respectively.

Figure 3:
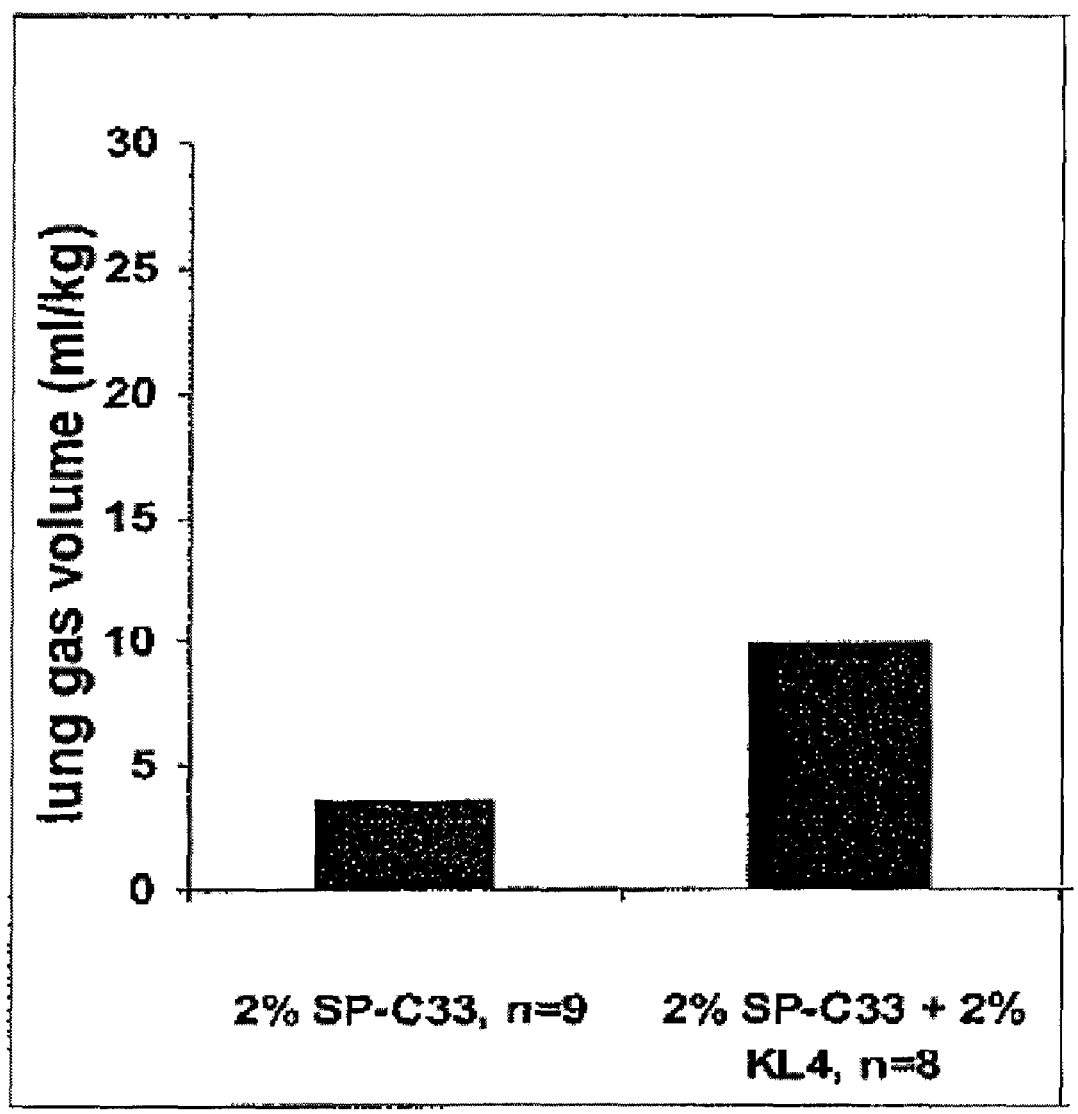
FIG. 3 shows the results in terms of lung gas volumes (ml/kg).

From FIG. 3 it can be appreciated that animals treated with the reconstituted surfactant preparation containing 2% w/w SP-C33 in combination with 2% $KL_4$ had higher lung gas volumes than animals that received 2% w/w SP-C33, indicating that addition of 2% w/w $KL_4$ to SP-C33 surfactant produced an increment in lung gas volumes.

Said result demonstrates that the reconstituted surfactant of the invention provides better stabilization of the phospholipid film in the alveoli at the end of expiration than a reconstituted surfactant preparation comprising only an analog of the protein SP-C.

Moreover FIG. 4 shows that the claimed reconstituted surfactant preparation significantly improves the respiratory function as expressed by the tidal volumes Obviously, numerous modifications and variations of the present invention are possible in light of the above teachings. It is therefore to be understood that, within the scope of the appended claims, the invention may be practiced otherwise than as specifically described herein.

What we claim is:

1. A reconstituted surfactant comprising
   (a) a lipid carrier;
   (b) an analog of the native surfactant protein SP-C represented by formula (Ic):

IPSSPVHLKRLKLLLLLLLLILLLILGALLΩ$_p$G$_p$L$_p$   (Ic)   (SEQ ID NO: 13)

wherein Ω is an amino acid residue selected from the group consisting of M or M oxidized on the sulfur atom, I, L, and nL, and p is 0 or 1; and
   (c) a polypeptide represented by the formula:

KLLLLKLLLLKLLLLKLLLLK.   (SEQ ID NO:6)

2. The reconstituted surfactant according to claim 1, wherein the analog of the native surfactant protein SP-C is selected from the group consisting of:

IPSSPVHLKRLKLLLLLLLLILLLILGALLMGL    (SEQ ID NO: 1)
   IPSSPVHLKRLKLLLLLLLLILLLILGALLIGL    (SEQ ID NO: 2)
   IPSSPVHLKRLKLLLLLLLLILLLILGALLLGL    (SEQ ID NO: 3)
   IPSSPVHLKRLKLLLLLLLLILLLILGALLnLGL,  (SEQ ID NO: 4)
   and
   IPSSPVHLKRLKLLLLLLLLILLLILGALL.      (SEQ ID NO: 5)

3. The reconstituted surfactant according to claim 1 wherein the analog of the native surfactant protein SP-C has the formula IPSSPVHLKRLKLLLLLLLLILLLIL-GALLLGL (SEQ ID NO: 3); and the polypeptide comprising a sequence of repeated units has the formula KLLLLKLLLLKLLLLKLLLLK (SEQ ID NO:6).

4. The reconstituted surfactant according to claim 1, wherein each component (b) and component (c) is present in an amount ranging from 0.5 to 10% based on the weight of the surfactant (w/w).

5. The reconstituted surfactant according to claim 1, wherein each component (b) and component (c) is present in an amount ranging from 1 to 5% based on the weight of the surfactant (w/w).

6. The reconstituted surfactant according to claim 1, wherein each component (b) and component (c) is present in an amount ranging from 1 to 3% based on the weight of the surfactant (w/w).

7. The reconstituted surfactant according to claim 1, wherein the lipid carrier is at least one phospholipid selected from the group consisting of a phosphatidylcholine, a phosphatidylglycerol, a phosphatidylinositol, a phosphatidylethanolamine, a phosphatidylserine, and a sphingomyelin.

8. The reconstituted surfactant according to claim 1, wherein the lipid carrier comprises a mixture of phospholipids.

9. The reconstituted surfactant according to claim 8, wherein the mixture of phospholipids consists of (a) dipalmitoylphosphatidylcholine and (b) a palmitoyloleoylphospholipid selected from the group consisting of palmitoyloleoylphosphatidylglycerol and a mixture of palmitoyloleoylphosphatidylglycerol with palmitoyloleoylphosphatidylcholine, in a weight ratio ranging from 95:5 to 50:50.

10. The reconstituted surfactant according to claim 9, wherein the phospholipid mixture consists of dipalmitoylphosphatidylcholine and palmitoyloleoylphosphatidylglycerol in a weight ratio of 68:31.

11. The reconstituted surfactant according to claim 9, wherein the (a) is in an amount ranging from 90 to 99% by weight based on the total weight of the surfactant, and the sum of (b) and (c) ranges from 1 to 10% by weight based on the total weight of the surfactant.

12. A pharmaceutical composition comprising the reconstituted surfactant according to claim 1 and a pharmaceutically acceptable carrier or excipient.

13. The pharmaceutical composition according to claim 12, which is in the form of a solution, dispersion, suspension or dry powder.

14. The pharmaceutical composition according to claim 12, which is in the form of an aqueous suspension.

15. The pharmaceutical composition according to claim 12, comprising the reconstituted surfactant in a concentration ranging from 2 and 160 mg/ml.

16. The pharmaceutical composition according to claim 12, comprising the reconstituted surfactant in a concentration ranging from 20 and 80 mg/ml.

17. A method of treating respiratory distress syndrome (RDS) in prematurely born babies comprising administering to a subject in need thereof an effective amount of the reconstituted surfactant according to claim 1.

18. A method of treating a disease related to a surfactant-deficiency or dysfunction selected from the group consisting of acute lung injury (ALI), RDS in adults (ARDS), meconium aspiration syndrome (MAS), and bronchopulmonary dysplasia (BPD) comprising administering to a subject in need thereof an effective amount of the reconstituted surfactant according to claim 1.

19. A method of preventing respiratory distress syndrome (RDS) in prematurely born babies comprising administering to a subject in need thereof an effective amount of the reconstituted surfactant according to claim 1.

* * * * *